US009032800B2

(12) United States Patent
Nakajima et al.

(10) Patent No.: US 9,032,800 B2
(45) Date of Patent: May 19, 2015

(54) PHOTOACOUSTIC IMAGING APPARATUS AND PHOTOACOUSTIC IMAGING METHOD

(71) Applicant: CANON KABUSHIKI KAISHA, Tokyo (JP)

(72) Inventors: Takao Nakajima, Kawasaki (JP); Kazuhiko Fukutani, Yokohama (JP); Yasufumi Asao, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/154,504

(22) Filed: Jan. 14, 2014

(65) Prior Publication Data
US 2014/0128718 A1 May 8, 2014

Related U.S. Application Data

(63) Continuation of application No. 13/132,998, filed as application No. PCT/JP2009/006758 on Dec. 10, 2009, now abandoned.

(30) Foreign Application Priority Data

Dec. 11, 2008 (JP) .................................. 2008-316042

(51) Int. Cl.
G01N 21/00 (2006.01)
A61B 5/00 (2006.01)
G01N 21/17 (2006.01)

(52) U.S. Cl.
CPC ............. A61B 5/0095 (2013.01); A61B 5/0073 (2013.01); G01N 21/1702 (2013.01); G01N 2021/1706 (2013.01)

(58) Field of Classification Search
USPC ............ 73/587, 589, 596, 602, 606, 607, 618
See application file for complete search history.

(56) References Cited

U.S. PATENT DOCUMENTS 4,385,634 A 5/1983 Bowen
4,607,341 A * 8/1986 Monchalin ..................... 702/136
4,712,247 A * 12/1987 Swarte ............................ 381/96

(Continued)

FOREIGN PATENT DOCUMENTS

CN 1937956 A 3/2007
WO 2008143200 A 11/2008

OTHER PUBLICATIONS

Wang et al., "Biomedical Optics, Principles and Imaging", Journal of Biomedical Optics, Jul./Aug. 2008, pp. 049902-1-049902-2, vol. 13, No. 4, Wiley & Sons, Inc., Hoboken, NJ.

(Continued)

Primary Examiner — Laura Martin
Assistant Examiner — Samir M Shah
(74) Attorney, Agent, or Firm — Canon USA Inc. IP Division

(57) ABSTRACT

A photoacoustic imaging apparatus performs imaging of an optical absorber. The photoacoustic imaging apparatus includes a light source, a detector configured to detect an acoustic wave generated from the optical absorber that has absorbed energy of light emitted from the light source, and a signal processing unit configured to form an image of the optical absorber. The signal processing unit stores information indicating whether a rate of change in pressure of the acoustic wave detected by the detector is positive or negative before performing a waveform process on the acoustic wave.

15 Claims, 9 Drawing Sheets

(56) References Cited

U.S. PATENT DOCUMENTS

| | | | |
|---|---|---|---|
| 5,070,733 A * | 12/1991 | Nagata et al. | 73/602 |
| 5,512,715 A * | 4/1996 | Takewa et al. | 181/295 |
| 5,657,754 A * | 8/1997 | Rosencwaig | 600/316 |
| 5,713,356 A * | 2/1998 | Kruger | 600/407 |
| 5,840,023 A * | 11/1998 | Oraevsky et al. | 600/407 |
| 6,102,857 A * | 8/2000 | Kruger | 600/437 |
| 6,139,543 A * | 10/2000 | Esch et al. | 606/7 |
| 6,216,540 B1 * | 4/2001 | Nelson et al. | 73/633 |
| 6,292,682 B1 * | 9/2001 | Kruger | 600/407 |
| 6,309,352 B1 * | 10/2001 | Oraevsky et al. | 600/407 |
| 6,379,325 B1 * | 4/2002 | Benett et al. | 604/22 |
| 6,466,806 B1 * | 10/2002 | Geva et al. | 600/310 |
| 6,662,040 B1 * | 12/2003 | Henrichs et al. | 600/431 |
| 6,728,661 B1 * | 4/2004 | Cannelli et al. | 702/187 |
| 6,833,540 B2 * | 12/2004 | MacKenzie et al. | 250/214.1 |
| 6,846,288 B2 * | 1/2005 | Nagar et al. | 600/437 |
| 8,396,534 B2 * | 3/2013 | Fukutani et al. | 600/476 |
| 2003/0167002 A1 * | 9/2003 | Nagar et al. | 600/437 |
| 2005/0105095 A1 * | 5/2005 | Pesach et al. | 356/432 |
| 2005/0107694 A1 * | 5/2005 | Jansen et al. | 600/431 |
| 2005/0163711 A1 * | 7/2005 | Nycz et al. | 424/9.1 |
| 2005/0175540 A1 * | 8/2005 | Oraevsky et al. | 424/9.5 |
| 2005/0187471 A1 * | 8/2005 | Kanayama et al. | 600/437 |
| 2007/0299341 A1 * | 12/2007 | Wang et al. | 600/443 |
| 2008/0058638 A1 * | 3/2008 | Zhu et al. | 600/425 |
| 2008/0123083 A1 * | 5/2008 | Wang et al. | 356/73 |
| 2008/0173093 A1 * | 7/2008 | Wang et al. | 73/602 |
| 2008/0221647 A1 * | 9/2008 | Chamberland et al. | 607/88 |
| 2008/0306371 A1 * | 12/2008 | Fukutani et al. | 600/407 |
| 2009/0002685 A1 * | 1/2009 | Fukutani et al. | 356/72 |
| 2009/0054763 A1 * | 2/2009 | Wang et al. | 600/425 |
| 2010/0049044 A1 * | 2/2010 | Burcher | 600/437 |
| 2010/0191109 A1 * | 7/2010 | Fukutani et al. | 600/437 |
| 2010/0256496 A1 * | 10/2010 | Zhu | 600/459 |
| 2011/0021924 A1 * | 1/2011 | Sethuraman et al. | 600/463 |

OTHER PUBLICATIONS

Numerix-DSP: "Algorithms-Envelope Detection", Internet Citation [Online], May 31, 2008, p. 1 of 2.

* cited by examiner

PHOTOACOUSTIC IMAGING APPARATUS AND PHOTOACOUSTIC IMAGING METHOD

CROSS-REFERENCE TO RELATED APPLICATIONS

This application is a Continuation of co-pending U.S. patent application Ser. No. 13/132,998 filed Jun. 6, 2011, which is a National Phase application of International Application No. PCT/JP2009/006758, filed Dec. 10, 2009, which claims priority benefit of Japanese Patent Application No. 2008-316042, filed Dec. 11, 2008. This disclosures of the above-named applications are hereby incorporated by reference herein in their entirety.

TECHNICAL FIELD

The present invention relates to an imaging apparatus using a photoacoustic effect and to a photoacoustic imaging method.

BACKGROUND ART

In recent years, there has been suggested a method for obtaining a distribution of optical characteristic values in vivo at high resolution by using a characteristic of ultrasound, which is less likely to scatter in vivo compared to light.

According to PTL, a living body is irradiated with pulsed light generated by a fight source, an acoustic wave that is generated from biological tissue through energy absorption of the pulsed light is detected, and a signal corresponding to the detected acoustic wave is analyzed, whereby a distribution of optical characteristic values in vivo is obtained. The imaging using an acoustic wave obtained through irradiation of a living body with light is generally called photoacoustic imaging.

Regarding a photoacoustic imaging method, the following technique is known. That is, when a photoacoustic wave generated by irradiating a spherical optical absorber 10 with light is detected by an acoustic wave detector 20 as illustrated in FIG. 9A, N-shape acoustic pressure information illustrated in FIG. 9B is obtained if optical absorption of the optical absorber 10 is even (see NPL).

The value obtained by multiplying a time width of the N-shape waveform by sonic speed is a value in which the size of the optical absorber 10 (here, the diameter of the sphere) is reflected. Also, the time when the N-shape waveform is detected reflects position information of the optical absorber 10. Furthermore, in a case where the intensity of light that arrives at the optical absorber 10 is equal, the magnitude of a signal having the N-shape waveform is proportional to the absorption coefficient of the optical absorber 10.

As described above, in photoacoustic imaging, an image of optical absorber 10 is reconstructed by using data obtained from a photoacoustic wave.

In the above-described photoacoustic imaging performed by detecting ultrasound that is generated through optical absorption, a tissue having an optical absorption co-efficient higher than that of a medium around an optical absorber is imaged. For example, a blood vessel in a living body has an optical absorption coefficient higher than that of a surrounding medium. Imaging of a blood vessel has been studied.

As a method for processing a photoacoustic wave signal obtained from a detector, a waveform process such as envelope detection can be used. By performing an image formation process after the waveform process, all in vivo optical characteristic distribution can be imaged.

When photoacoustic wave signals measured by detectors provided at various positions are used, an in vivo optical characteristic distribution can be imaged by using image reconstruction using a method involving an aperture synthesis process, such as delay and sum, and a waveform process, such as envelope detection.

In the near-infrared region of about 700 to 1100 nm that is used in photoacoustic imaging, there is a tissue having an optical absorption coefficient higher than that of a surrounding tissue, such as a blood vessel, and also there is a tissue having an optical absorption coefficient lower than that of a surrounding tissue, such as a calcified substance.

For this reason, in an image formation method simply using envelope detection described above, the difference in optical absorption coefficient between a subject and a surrounding medium can be detected only in the form of an absolute value. Accordingly, it has been difficult to determine whether the optical absorption coefficient of the subject is higher or lower than that of the surrounding medium.

CITATION LIST

Patent Literature

PTL 1: U.S. Pat. No. 5,713,356

Non Patent Literature

NPL 1: L. V. Wang, et al. "Biomedical Optics-Principles and Imaging", Wiley, Ch. 12, 2007

SUMMARY OF INVENTION

The present invention provides a photoacoustic imaging apparatus and a photoacoustic imaging method that can perform imaging by distinguishing a tissue having an optical absorption coefficient lower than that of a surrounding medium and a tissue having an optical absorption coefficient higher than that of a surrounding medium from each other.

A photoacoustic imaging apparatus according to an aspect of the present invention includes a light source, a detector configured to detect an acoustic wave generated from an optical absorber that has absorbed energy of light emitted from the light source, and a signal processing unit configured to form an image of the optical absorber by storing information indicating whether a rate of change in pressure of the acoustic wave detected by the detector is positive or negative before performing a waveform process on the acoustic wave.

A photoacoustic imaging method according to an aspect of the present invention includes a step of emitting light from a light source, a step of detecting an acoustic wave generated from an optical absorber that has absorbed energy of the light emitted from the light source, and a step of storing information indicating whether a rate of change in pressure of the detected acoustic wave is positive or negative before performing a waveform process on the acoustic wave.

According to the aspects of present invention, a photoacoustic imaging apparatus and a photoacoustic imaging method that can perform imaging by distinguishing a tissue having an optical absorption coefficient lower than that of a surrounding medium and as tissue having an optical absorption coefficient higher than that of a surrounding medium from each other can be provided.

Other features and advantages of the present invention will be apparent from the following description taken in conjunc-

DESCRIPTION OF EMBODIMENT

Embodiments of the present invention will now be described in detail in accordance with the accompanying drawings.

Figure 2A:
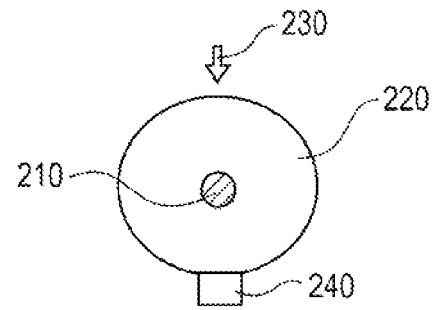
FIG. 2A is a diagram for explaining an imaging method for an optical absorber having an optical absorption coefficient higher than that of a background.
Figure 2B:
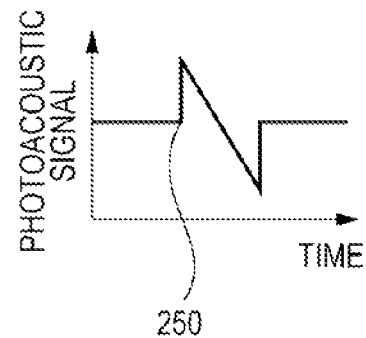
FIG. 2B is as diagram for explaining the imaging method for an optical absorber having an optical absorption coefficient higher than that of a background.

FIGS. 2A to 2D are diagrams for explaining an image processing method in a case where the optical absorption coefficient of a spherical tissue 210 is higher than that of a surrounding medium 220. As illustrated in FIG. 2A, when a photoacoustic wave that is generated by irradiating the tissue 210 with pulsed light 230 is detected by a detector 240, waveform data 250 illustrated in FIG. 2B is obtained. When light is evenly absorbed by an absorber, the waveform data is N shaped.

The method for processing that is performed thereafter has two alternatives.

Figure 2C:
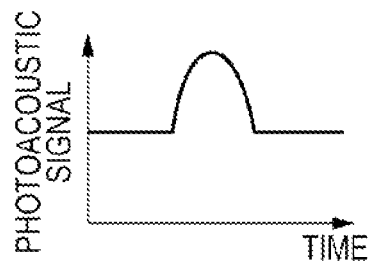
FIG. 2C is a diagram for explaining the imaging method for an optical absorber having an optical absorption coefficient higher than that of a background.
Figure 2D:
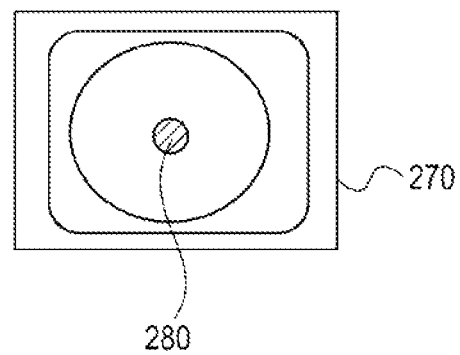
FIG. 2D is a diagram for explaining the imaging method for an optical absorber having an optical absorption coefficient higher than that of a background.

In one of them, a process based on envelope detection is performed on the waveform data illustrated in FIG. 2B, as illustrated in FIG. 2C. An image formation process is performed on the basis of the processed waveform data, and an image 280 of the optical absorber reflecting the optical absorption coefficient is displayed on a display unit 270 as illustrated in FIG. 2D.

In the other method, pieces of waveform data detected at various positions are added in an image reconstruction method using an algorithm of a synthetic aperture process or the like, envelope detection is then performed, and the image 280 of the optical absorber reflecting the optical absorption coefficient is displayed on the display unit 270.

On the other hand, FIGS. 3A to 3E are diagrams for explaining an image processing method in a case where the optical absorption coefficient of a spherical tissue 310 is lower than that of the surrounding medium 220.

The inventers of the present invention have found through study that, in such a case where the optical absorption coefficient of the tissue 310 is lower than that of the surrounding medium 220, data 350 having an N-shape waveform in which positive/negative is inverted with respect to the waveform illustrated in FIG. 2B (inverted. N-shape waveform) is detected, as illustrated in FIG. 3B.

That is, in a case where the optical absorption coefficient of a target portion is higher than that of a surrounding tissue, a photoacoustic wave signal rises at a signal start point (i.e., the rate of change in pressure is positive at the start). On the other hand, in a case where the optical absorption coefficient of a target portion is lower than that of a surrounding tissue, a photoacoustic wave signal falls at a signal start point (i.e., the rate of change in pressure is negative at the start).

The present invention has been made using the above-described findings, and is characterized in that imaging is performed with a tissue having an optical absorption coefficient lower than that of a surrounding medium being distinguished from a tissue having an optical absorption coefficient higher than that of a surrounding medium.

First Embodiment

Figure 1:
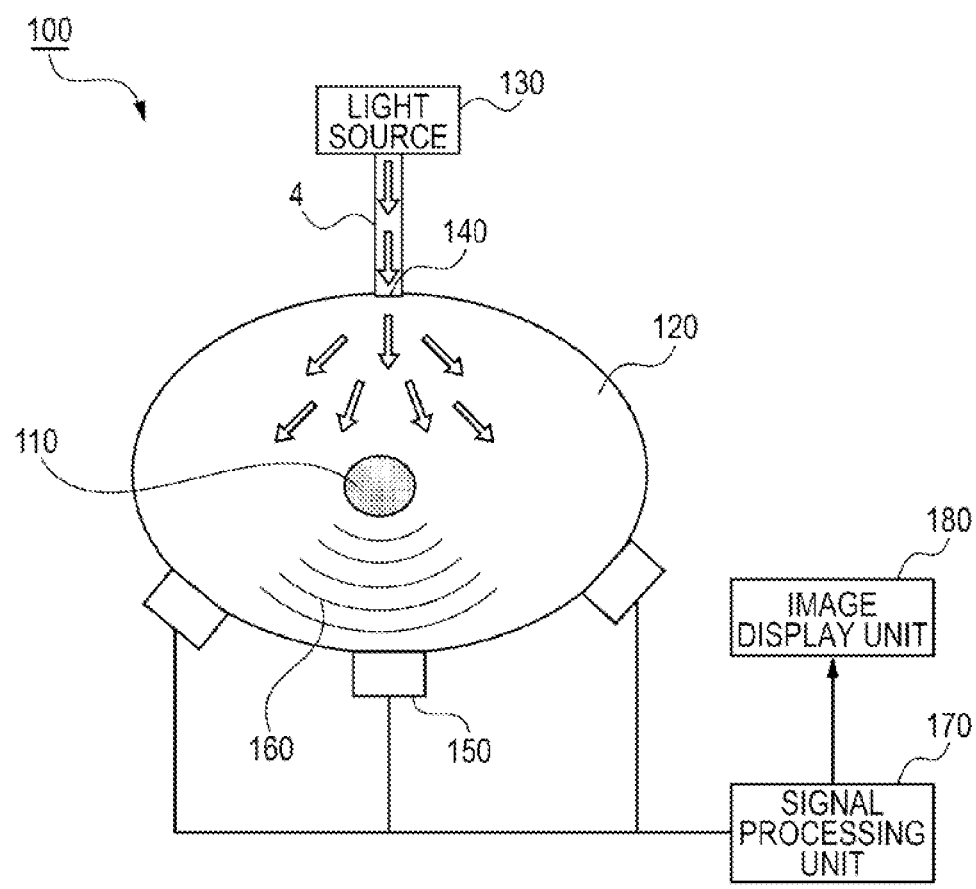
FIG. 1 illustrates an exemplary configuration of a photoacoustic imaging apparatus according to an embodiment of the present invention.

FIG. 1 illustrates an exemplary configuration of a photoacoustic imaging apparatus 100 according to a first embodiment of the present invention.

The photoacoustic imaging apparatus 100 according to this embodiment is capable of imaging optical characteristic values in vivo and a concentration distribution of substances constituting biological tissue obtained from information about those values for the purpose of diagnosing a malignant tumor, a blood vessel disease, and the like, or observing a progress of chemical treatment. Particularly, the photoacoustic imaging apparatus 100 is capable of imaging an optical absorber having an optical absorption coefficient lower than that of a surrounding medium.

In the photoacoustic imaging apparatus 100 according to this embodiment, light emitted from a light source 130 propagates through an optical fiber 140, so that a living body 120 is irradiated with the light. The living body 120 as a surrounding medium has an optical absorber 110. Light energy absorbed by the optical absorber 110 is converted into an acoustic wave 160. The acoustic wave 160 is detected by detectors 150. The optical absorber 110 generates an acoustic wave in accordance with a difference in optical absorption coefficient between the optical absorber 110 and a surrounding medium even in a case where the optical absorption coefficient of the optical absorber 110 is lower than that of a surrounding medium constituting a subject.

Also, the photoacoustic imaging apparatus 100 according to this embodiment includes a signal processing unit 170 that obtains distribution information about optical characteristic values by using electric signals obtained from the detectors 150.

The light source 130 generates pulsed light. The pulsed light is in an order of several nanoseconds to several hundreds of nanoseconds, and the wavelength thereof should be 700 nm or more and 1100 mn or less. A laser is used as the light source 130, but a light-emitting diode or the like can be used in place of the laser. When a dye laser or an OPO (Optical Parametric Oscillator) capable of converting an oscillation wavelength is used, a difference in distribution of optical characteristic values due to the wavelength can be measured.

Each of the detectors 150 absorbs energy of light with which the living body 120 is irradiated, detects an acoustic wave that is generated from the optical absorber 110 in the living body 120 in accordance with a difference in optical absorption coefficient, and converts the acoustic wave into an electric signal. As the detector 150, a focus transducer capable of receiving only an acoustic wave generated from a specific region can be used. When the focus transducer is used, the position of an optical absorber can be specified, so that a process of image reconstruction, such as delay and sum, is not necessarily performed. Also, any type of acoustic wave detector may be used as the detector 150 as long as the detector is capable of detecting an acoustic wave signal, for example, a transducer using a piezoelectric phenomenon, a transducer using optical resonance, or a transducer using a change in capacitance. In this embodiment, the plurality of detectors 150 are placed on a surface of the living body 120. Alternatively, a single detector may be used to scan the surface of the living body 120.

The signal processing unit 170 analyzes the electric, signal, whereby distribution information about optical characteristic values of the living body 120 is obtained. As the signal processing unit 170, any device may be used as long as the intensity and time change of an acoustic wave can be stored and converted into data of a distribution of optical characteristic values by using a computing unit. For example, an oscilloscope and a computer capable of analyzing data stored in the oscilloscope can be used.

In a case of the spherical tissue 210 illustrated in FIG. 2A, a photoacoustic signal generated from the tissue 210 having an optical absorption coefficient higher than that of the surrounding medium 220 rises at the start point as illustrated in FIG. 2B (N-shape waveform).

Figure 3A:
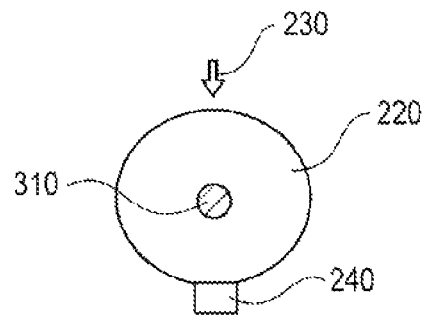
FIG. 3A is a diagram for explaining an imaging method for an optical absorber having an optical absorption coefficient lower than that of a background.
Figure 3B:
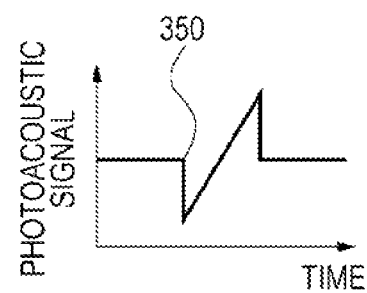
FIG. 3B is a diagram for explaining the imaging method for an optical absorber having an optical absorption coefficient lower than that of a background.

On the other hand, in a case of the spherical tissue 310 illustrated in FIG. 3A having an optical absorption coefficient lower than that of the surrounding medium 220, the signal falls at the start point as illustrated in FIG. 3B (inverted N-shape waveform).

Figure 4:
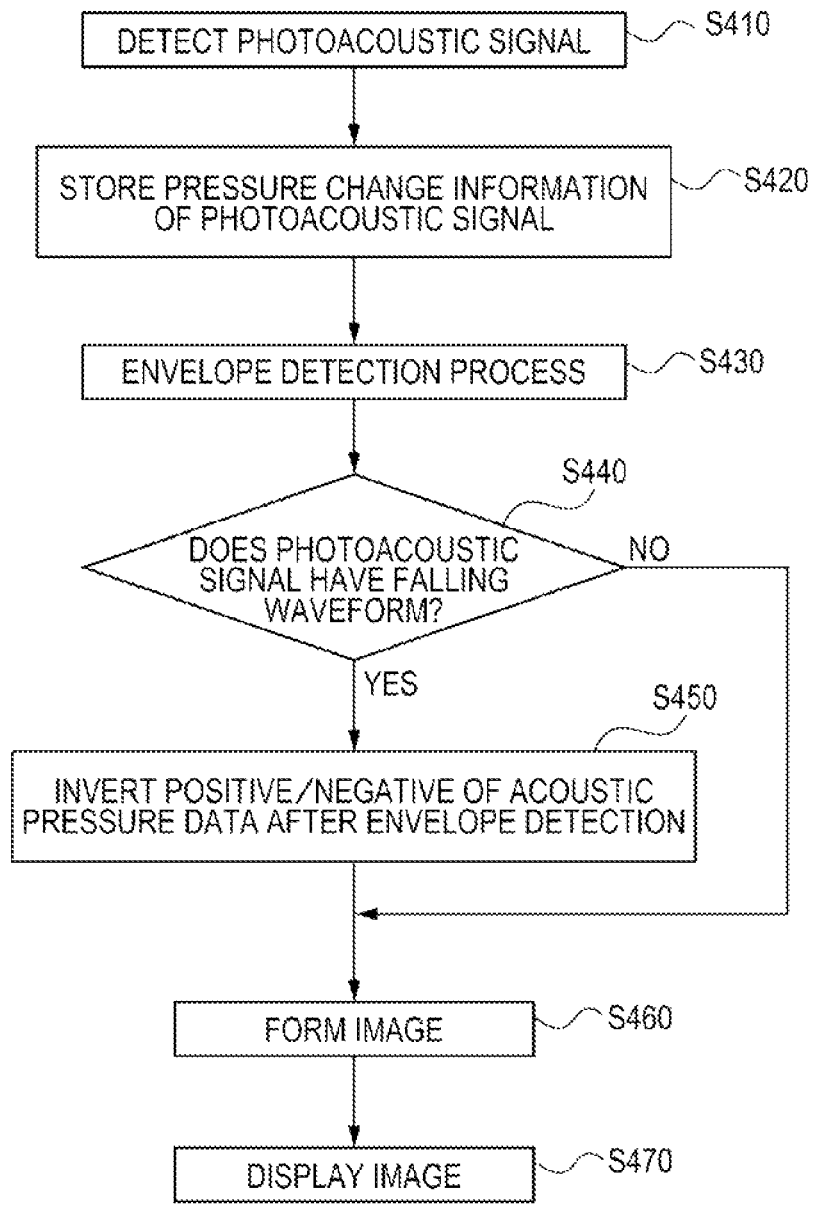
FIG. 4 is a flowchart according to a first embodiment.

A description will be given with reference to the flowchart in FIG. 4 about a signal processing method for imaging a tissue having an optical absorption coefficient lower than that of a surrounding medium on the basis of the above-described findings.

First, a focus transducer serving as the detector 150 detects a photoacoustic signal S410).

Figure 3C:
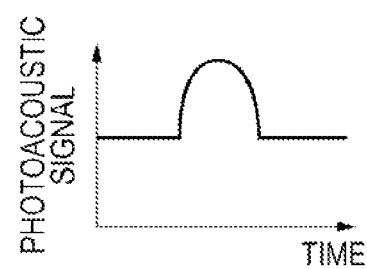
FIG. 3C is a diagram for explaining the imaging method for an optical absorber having an optical absorption coefficient lower than that of a background.
Figure 3D:
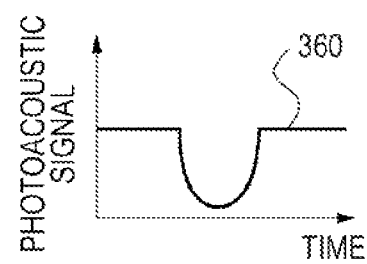
FIG. 3D is a diagram for explaining the imaging method for an optical having an optical absorption coefficient lower than that of a background.

Subsequently, the signal processing unit 170 stores information indicating whether the rate of change in pressure of the photoacoustic signal has a positive value or a negative value (S420). In order to adapt the data of the photoacoustic signal to an absorption characteristic of an optical absorber, an envelope detection process (e.g., absolute value is obtained after Hilbert transform) is performed as a waveform process (S430). Examples of acoustic pressure information obtained through the envelope detection process are illustrated in FIGS. 2C and 3C.

Subsequently, it is determined whether the photoacoustic signal rises at the signal start point in change in pressure of the photoacoustic signal (S440). Depending on the characteristic of the detector used, correction should be performed before determination in accordance with a frequency response characteristic of the detector. That is, deconvolution should be performed on the received photoacoustic signal in accordance with the frequency response characteristic of the detector used.

Here, if it is determined in S440 that the photoacoustic signal rises, image formation is performed in the same manner as in a conventional photoacoustic imaging apparatus (S460). On the other hand, if it is determined in step S440 that the photoacoustic signal falls, the positive/negative of acoustic pressure data after envelope detection is inverted (S450). With this process in S450, the waveform data 360 illustrated in FIG. 3D can be obtained. Subsequently, image formation is performed in the same manner as in the case where the signal rises (S460). In order to perform image formation, time data of the waveform data 360 may be converted into position data and then be plotted.

Figure 3E:
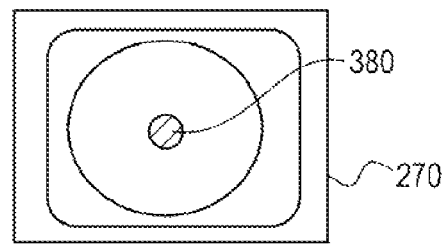
FIG. 3E is a diagram for explaining the imaging method for an optical a absorber having an optical absorption coefficient lower than that of a background.

Finally, the signal of an image obtained in S460 is output from the signal processing unit 170, whereby the image of the optical absorber is displayed on the image display units 180 and 270. In this case, as illustrated in FIGS. 2D and 3E, the image 280 of the tissue having an optical absorption coefficient higher than that of the surrounding tissue and the image 380 of the tissue having an optical absorption coefficient lower than that of the surrounding tissue can be displayed on the image display unit 270 in different display forms. In order to express different types of tissues having different optical absorption coefficients, different display colors or different color tones can be used (e.g., gradation is changed). Alternatively, an identification symbol (e.g., + or −) may be given to a tissue having an optical absorption coefficient higher or lower than that of a surrounding tissue.

The use of the photoacoustic imaging apparatus 100 according to the first embodiment enables imaging of not only a tissue having an optical absorption coefficient higher than that of a surrounding medium in vivo but also a tissue having an optical absorption coefficient lower than that of a surrounding medium even when envelope detection is used.

It is known that the optical absorption coefficient of a substance varies in accordance with the wavelength of light. In a case where light of a plurality of wavelengths is used, optical absorption coefficients in vivo for the respective wavelengths are calculated. Then, those coefficients are compared with the wavelength dependency unique to substances constituting biological tissue (glucose, collagen, oxidation-reduction hemoglobin, etc.), so that a concentration distribution of the substances constituting a living body can be imaged.

Furthermore, in a case when measurement is performed with a plurality of wavelengths by using the photoacoustic imaging apparatus 100 according to this embodiment, a high/low relationship between the optical absorption coefficient of a substance and that of a surrounding medium can be determined, so that the substance as a measurement target can be specified.

Now, a description will be given about an example of determining the existence of substances A, B, and C, the optical absorption coefficient thereof being different from that of a surrounding medium. Assume that the optical absorption coefficient of the substance A is higher than that of a surrounding medium in both of certain two wavelengths lambda-1 and lambda-2. Also, assume that the optical absorption coefficient of the substance B is higher in the wavelength lambda-1 and is lower in the wavelength lambda-2. Also, assume that the optical absorption coefficient of the substance C is lower in both of the wavelengths lambda-1. and lambda-2.

In this case, when measurement is performed by using the two wavelengths lambda-1 and lambda-2, a positive signal (a signal that rises at the signal start point) is output from the substance A in the both wavelengths. As for the substance B, a positive signal is obtained when the wavelength lambda-1 is used, whereas a negative signal (a signal that falls at the signal start point) is output when the wavelength lambda-2 is used. As for the substance C, a negative signal is output in the both wavelengths. By comparing these results, the substances A, B, and C can be distinguished from each other.

As described above, by using the photoacoustic imaging apparatus including the light source capable of emitting light of a plurality of wavelengths and the signal processing unit, the substances A, B, and C can be identified or a distribution of the substances A, B, and C can be easily determined on the basis of a positive/negative value of an image reconstruction result.

That is, the comparison between the shape of a first acoustic wave obtained through irradiation with light of the wavelength lambda-1 and the shape of a second acoustic wave obtained through irradiation with light of the wavelength lambda-2 enables analysis of a substance. Such a process can be performed by the above-described signal processing unit 170 or another unit.

Second Embodiment

A photoacoustic imaging apparatus according to a second embodiment is different from the photoacoustic imaging apparatus 100 according to the first embodiment in that an image formation process is performed after a normal envelope detection process has been performed. That is, in the first embodiment, image formation is performed after the positive/negative of acoustic pressure data after envelope detection has been inverted. On the other hand, in the second embodiment, image formation is performed without performing such a process. The configuration of the apparatus according to the second embodiment is the same as that of the first embodiment except for signal processing and image reconstruction, and thus the description thereof is omitted.

Figure 5:
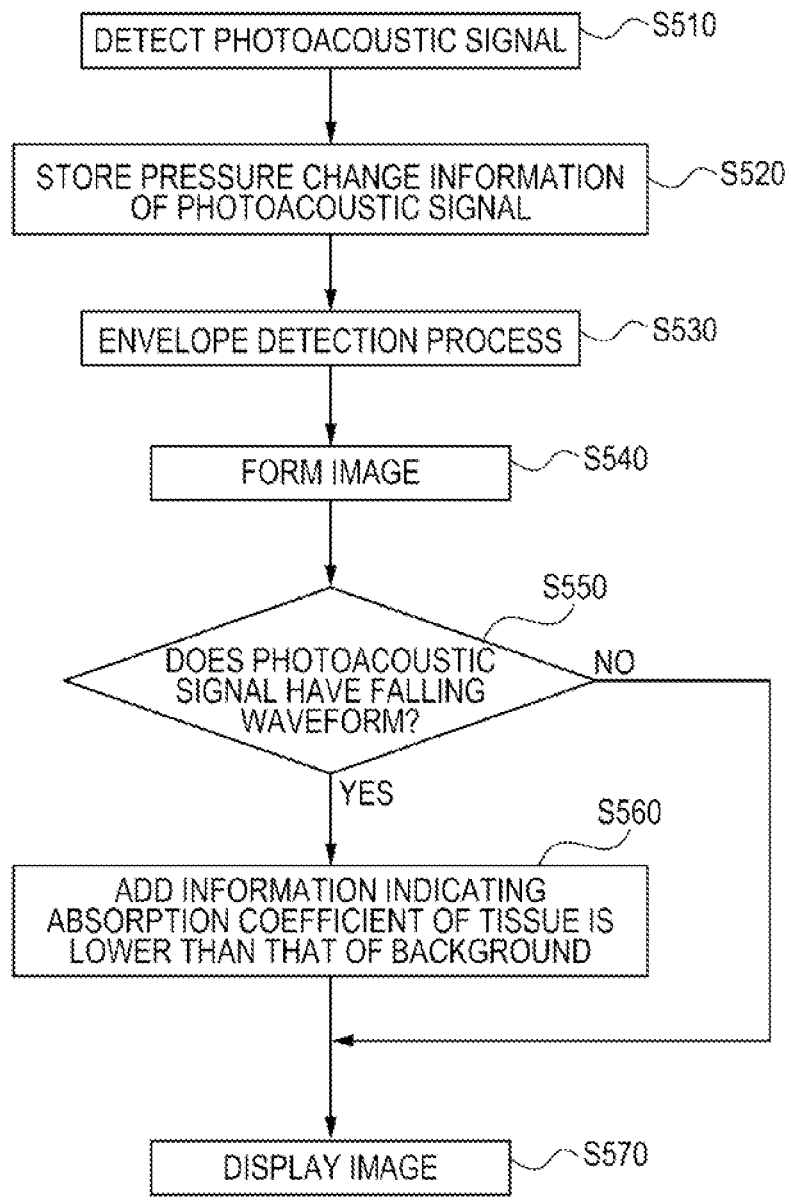
FIG. 5 is a flowchart according to a second embodiment.

FIG. 5 is a flowchart of signal processing and image reconstruction according to the second embodiment.

First, a focus transducer serving as the detector 150 detects a photoacoustic signal (S510).

Subsequently, the signal processing unit 170 stores pressure change information of the photoacoustic signal (S520). After an envelope detection process has been performed to adapt the data of the photoacoustic signal to an absorption characteristic of an optical absorber (S530), an image formation process is performed (S540). In the image formation process, time data of the waveform data 360 is converted into position data and is plotted.

In the image formation process according to the first embodiment, image reconstruction is performed after the positive/negative of the data obtained through envelope detection has been inverted when a fall at the signal start point is detected. However, according to the second embodiment, the image formation process is performed without inversion of the positive/negative of data obtained through envelope detection.

Subsequently, it is determined whether the photoacoustic signal falls on the basis of the pressure change information of the photoacoustic signal stored in S520 (S550). Depending on the characteristic of the detector used, correction should be performed in accordance with the frequency response characteristic of the detector before determination.

If it is determined in S550 that the photoacoustic signal rises, the image obtained in S540 is displayed on the image display units 180 and 270 (S570).

On the other hand, if it is determined in S550 that the photoacoustic signal falls, information indicating that the optical absorption coefficient of the tissue is lower than that of a background is added (S560). After that, the signal of an image added with the information is output from the signal processing unit 170 and the image is displayed on the image display units 180 and 270 (S570).

Accordingly, an image of a tissue having an optical absorption coefficient higher than that of a surrounding tissue and an image of a tissue having an optical absorption coefficient lower than that of a surrounding tissue can be displayed in different display forms. In order to express different types of tissues having different optical absorption coefficients, different display colors or different color tones can be used. Alternatively an identification symbol may be given to a tissue having an optical absorption coefficient lower than that of a surrounding tissue.

In the photoacoustic imaging apparatus according to the second embodiment, as in the apparatus according to the first embodiment, a substance as a measurement target can be specified by using light of a plurality of wavelengths.

Third Embodiment

A photoacoustic imaging apparatus according to a third embodiment is different from the photoacoustic imaging apparatuses according to the first and second embodiments in that image reconstruction is performed by using an algorithm based on delay and or an algorithm based on Fourier transform. As a detector according to this embodiment, a detector capable of detecting signals from various regions should be used. Other than the foregoing points, the configuration of the apparatus according to the third embodiment is the same as that according to the first embodiment, and thus the description thereof is omitted.

Figure 6:
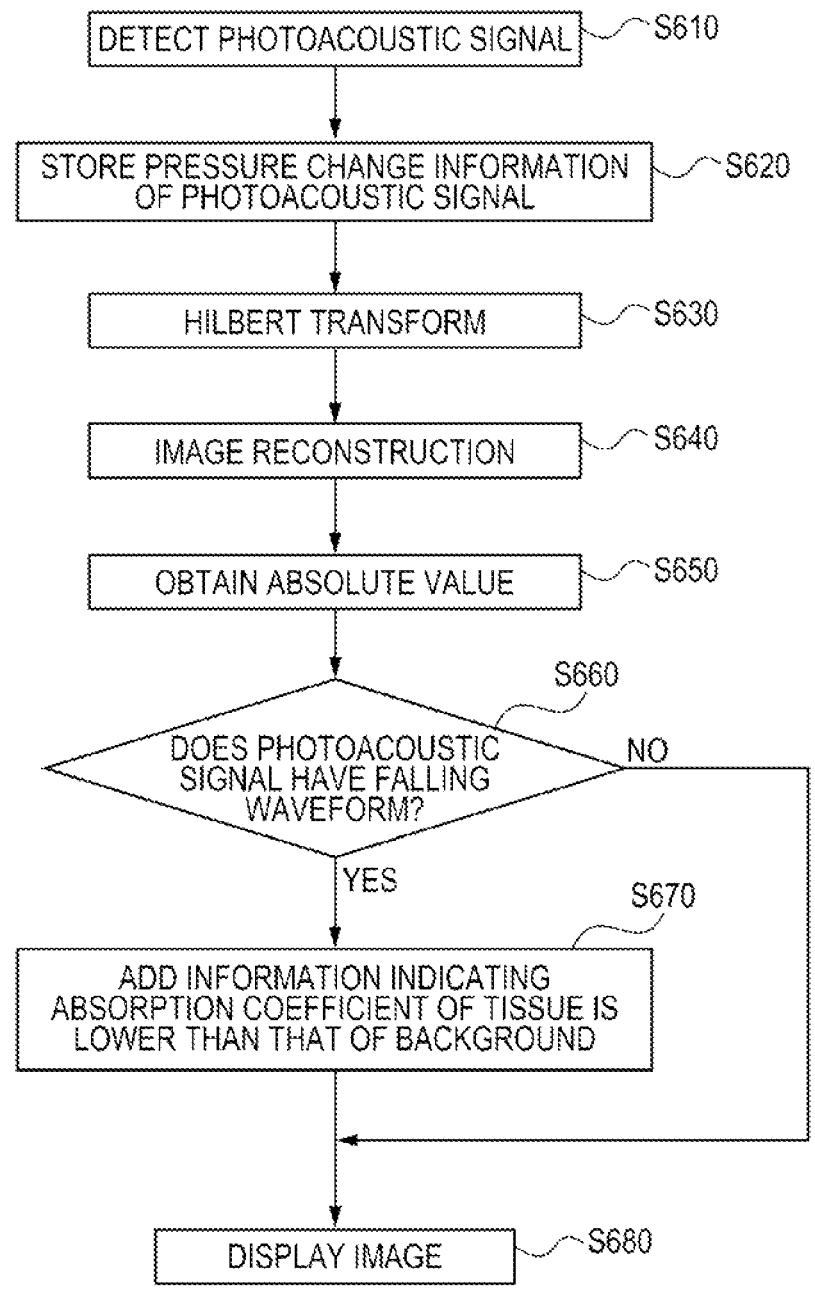
FIG. 6 is a flowchart according to a third embodiment.

FIG. 6 is a flowchart of signal processing and image reconstruction according to the third embodiment.

First, the detector 150 detects a photoacoustic signal (S610).

Subsequently, the signal processing unit 170 stores pressure change information of the photoacoustic signal (S620), performs Hilbert transform on data of the photoacoustic signal (S630), and performs image reconstruction (S640). As a method for the image reconstruction, an algorithm based on delay and sum or an algorithm based on Fourier transform is used. After that, an absolute value of the obtained image data is obtained (S650).

Subsequently, it is determined whether the photoacoustic signal falls on the basis of the pressure change information of the photoacoustic signal stored in S620 (S660). Depending on the characteristic of the detector used, correction should be performed in accordance with the frequency response characteristic of the detector before determination.

If it is determined in S660 that the photoacoustic signal rises, the obtained signal of an image is output from the signal processing unit 170 and the image is displayed on the image display units 180 and 270 (S680).

On the other hand, if it is determined in S660 that the photoacoustic signal falls, information indicating that the optical absorption coefficient of the tissue is lower than that of a background is added (S670). After that, the signal of an image added with the information is output from the signal processing unit 170 and the image is displayed on the image display units 180 and 270 (S680).

Accordingly, an image of a tissue having an optical absorption coefficient higher than that of surrounding tissue and an image of a tissue having an optical absorption coefficient lower than that of a surrounding tissue can be displayed in different display forms. In order to express different types of tissues having different optical absorption coefficients, different display colors or different color tones can be used. Alternatively, an identification symbol (e.g., + or −) may be given.

Alternatively, the data obtained through image reconstruction after envelope detection may be displayed on the image display units 180 and 270 by inverting positive/negative of the optical absorption coefficient of the optical absorber.

In the photoacoustic imaging apparatus according to the third embodiment, as in the apparatus according to the first embodiment, a substance as it measurement target can be specified by using light of a plurality of wavelengths.

Example 1

Simulation was performed for a photoacoustic signal obtained in the following cases: a case where the optical absorption coefficient of a measurement target is higher than that of a surrounding tissue constituting a subject; and a case where the optical absorption coefficient of a measurement target is lower than that of a surrounding tissue constituting a subject.

Figure 7A:
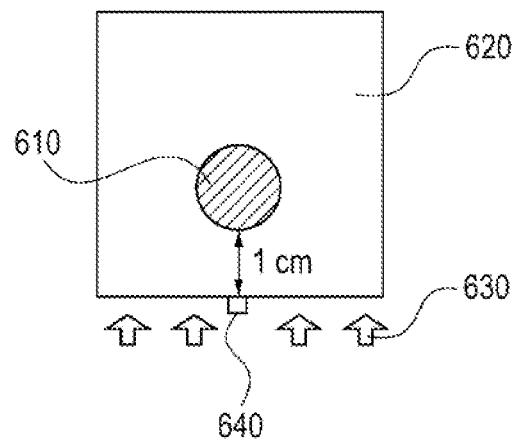
FIG. 7A is a diagram for explaining a simulation model according to an example of the present invention.
Figure 7B:
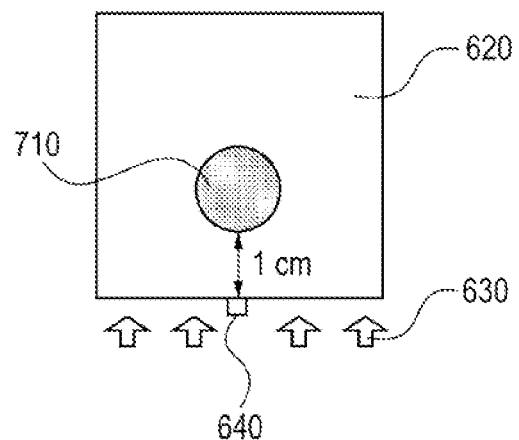
FIG. 7B is a diagram for explaining the simulation model according to the example of the present invention.

A simulation model is illustrated in FIGS. 7A and 7B. Specifically, a two-dimensional space was set and simulation was performed for a photoacoustic signal that is obtained at a point 640 when irradiation with light 630 from the bottom of the figure was performed. An optical absorber 610 as a measurement target, which is a circle having a diameter of 1 cm, was positioned at 1 cm from a light irradiation point. The sonic speed was 1500 m/s.

The optical absorption coefficient of a background region 620 was 0.1 $cm^{-1}$, and the equivalent scattering coefficient thereof was 10 $cm^{-1}$. The optical absorption coefficient of the optical absorber 610 was 1.0 $cm^{-1}$, and the equivalent scattering coefficient thereof was 10 $cm^{-1}$. The optical absorption coefficient of an optical absorber 710 was 0 $cm^{-1}$, and the equivalent scattering coefficient thereof was 10 $cm^{-1}$.

Figure 8A:
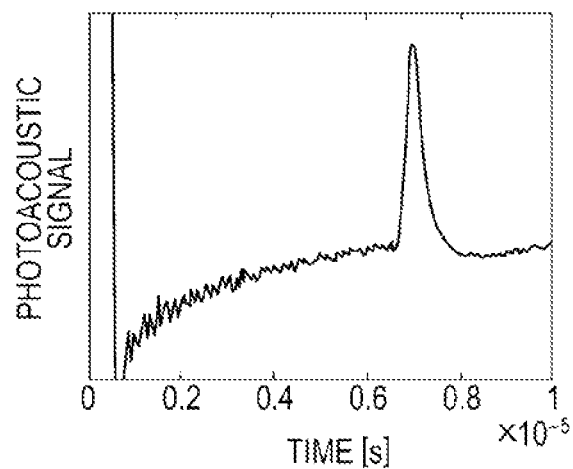
FIG. 8A is a diagram for explaining a simulation result according to the example of the present invention.
Figure 8B:
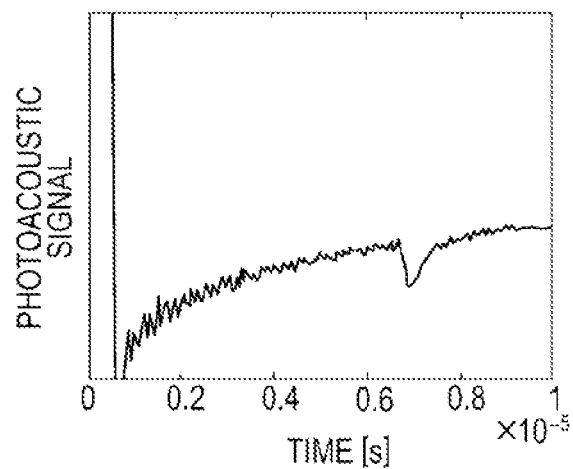
FIG. 8B is a diagram for explaining the simulation result according to the example of the present invention.
Figure 9A:
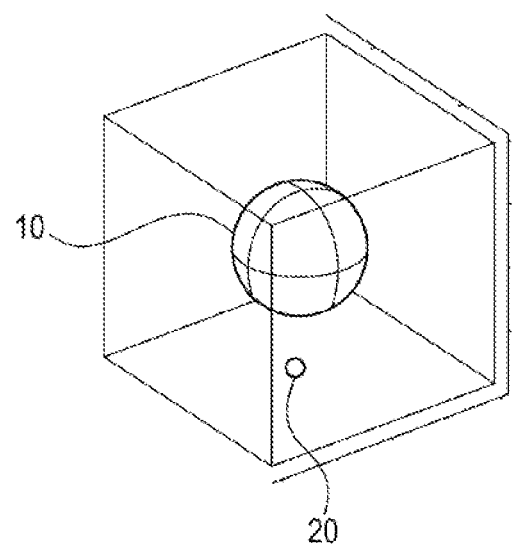
FIG. 9A is a diagram for explaining a photoacoustic signal having an N-shape waveform.
Figure 9B:
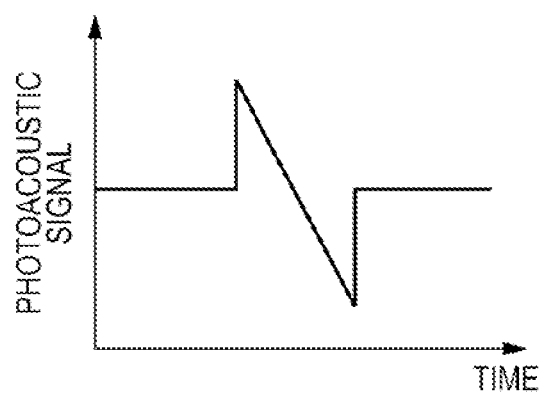
FIG. 9B is a diagram for explaining the photoacoustic signal having an N-shape waveform.

A simulation result about a time-lapse change of acoustic pressure at the point 640 is illustrated in FIGS. 8A and 8B. In the case of the optical absorber 610 having an optical absorption coefficient higher than that of the region 620, a positive photoacoustic signal in which a signal from a measurement target rises at the start point was obtained (FIG. 8A). On the other hand, in the case of the optical absorber 710 having an optical absorption coefficient lower than that of the region 620, a negative photoacoustic signal in which a signal from a measurement target falls at the start point was obtained (FIG. 8B).

Accordingly, it is understood that at positive photoacoustic signal that rises at the start point is generated when the optical absorption coefficient is higher than that of a surrounding region and that a negative photoacoustic signal that falls at the start point is generated when the optical absorption coefficient is lower than that of a surrounding region.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A photoacoustic imaging apparatus comprising:
    a light source;
    a detector configured to convert an acoustic wave into an electric signal, the acoustic wave being generated from an optical absorber as a measurement target by irradiating the measurement target with light emitted from the light source; and
    a signal processing unit configured to obtain an image of the measurement target based on the electric signal,
    wherein the signal processing unit is configured to determine whether an optical absorption coefficient of the optical absorber is lower or higher than an optical absorption coefficient of a surrounding region of the optical absorber based on the electric signal and obtain the image based on a result of the determination.

2. The photoacoustic imaging apparatus according to claim 1, wherein
    the signal processing unit is configured to determine whether the optical absorption coefficient of the optical absorber is lower or higher than the optical absorption coefficient of the surrounding region of the optical absorber based on change in pressure of the acoustic wave.

3. The photoacoustic imaging apparatus according to claim 2, wherein,
    in a case where the change in pressure of the acoustic wave is negative at the start, the signal processing unit is configured to determine that the optical absorption coefficient of the optical absorber is lower than the optical absorption coefficient of the surrounding region of the optical absorber.

4. The photoacoustic imaging apparatus according to claim 2, wherein,
    in a case where the change in pressure of the acoustic wave is positive at the start, the signal processing unit is configured to determine that the optical absorption coefficient of the optical absorber is higher than the optical absorption coefficient of the surrounding region of the optical absorber.

5. The photoacoustic imaging apparatus according to claim 1, wherein
    the signal processing unit is configured to obtain the image with a display color based on the result of the determination.

6. The photoacoustic imaging apparatus according to claim 1, wherein
    the signal processing unit is configured to obtain the image with a color tone based on the result of the determination.

7. The photoacoustic imaging apparatus according to claim 1, wherein
    the signal processing unit is configured to obtain the image with an identification symbol based on the result of the determination.

8. The photoacoustic imaging apparatus according to claim 1, wherein
    the signal processing unit is configured to cause an image display unit to display information indicating whether the optical absorption coefficient of the optical absorber is lower or higher than the optical absorption coefficient of the surrounding region of the optical absorber.

9. The photoacoustic imaging apparatus according to claim 1, wherein,
in a case where the optical absorption coefficient of the optical absorber is lower than the optical absorption coefficient of the surrounding region of the optical absorber, the signal processing unit is configured to perform a waveform process on the electric signal, convert a sign of the electric signal after performing the waveform process from a positive value to a negative value or vice versa, and obtain the image based on the electric signal whose sign is converted.

10. The photoacoustic imaging apparatus according to claim 9, wherein the waveform process is envelope detection.

11. The photoacoustic imaging apparatus according to claim 1, wherein the detector is a focus transducer.

12. The photoacoustic imaging apparatus according to claim 1, wherein
the signal processing unit is configured to perform correction of the electric signal in accordance with a frequency response of the detector, and
after performing the correction, the signal processing unit is configured to determine whether the optical absorption coefficient of the optical absorber is lower or higher than the optical absorption coefficient of the surrounding region of the optical absorber based on the electric signal.

13. The photoacoustic imaging apparatus according to claim 1, wherein
the signal processing unit is configured to obtain the image regarding a distribution of optical characteristic value in the measurement target.

14. The photoacoustic imaging apparatus according to claim 1, wherein
the signal processing unit is configured to obtain the image regarding a concentration distribution of a substance constituting the measurement target.

15. A photoacoustic imaging method comprising:
a step of emitting light from a light source;
a step of converting an acoustic wave into an electric signal, the acoustic wave being generated from an optical absorber as a measurement target by irradiating the measurement target with the light emitted from the light source;
a step of determining whether an optical absorption coefficient of the optical absorber is lower or higher than an optical absorption coefficient of a surrounding region of the optical absorber based on the electric signal; and
a step of obtaining an image of the measurement target using a result of the determination and the electric signal.

* * * * *